United States Patent
Lau (10) Patent No.: US 11,733,168 B2
(45) Date of Patent: Aug. 22, 2023

(54) SENSOR MODULE FOR MULTIPARAMETRICALLY ANALYSING A MEDIUM

(71) Applicant: SENTRONIC GMBH—GESELLSCHAFT FÜR OPTISCHE MEßSYSTEME, Dresden (DE)

(72) Inventor: Matthias Lau, Dresden (DE)

(73) Assignee: SENTRONIC GMBH—GESELLSCHAFT FÜR OPTISCHE MESSSYSTEME, Dresden (DE)

( * ) Notice: Subject to any disclaimer, the term of this patent is extended or adjusted under 35 U.S.C. 154(b) by 0 days.

(21) Appl. No.: 17/621,630

(22) PCT Filed: Jun. 8, 2020

(86) PCT No.: PCT/EP2020/065837
§ 371 (c)(1),
(2) Date: Dec. 21, 2021

(87) PCT Pub. No.: WO2020/259996
PCT Pub. Date: Dec. 30, 2020

(65) Prior Publication Data
US 2022/0205924 A1 Jun. 30, 2022

(30) Foreign Application Priority Data
Jun. 25, 2019 (DE) .......... 102019117045.1

(51) Int. Cl.
*G01N 21/77* (2006.01)
*C12M 1/00* (2006.01)
(Continued)

(52) U.S. Cl.
CPC ............ *G01N 21/77* (2013.01); *C12M 23/28* (2013.01); *C12M 41/00* (2013.01); *C12M 41/12* (2013.01);
(Continued)

(58) Field of Classification Search
CPC ................. G01N 21/77; G01N 21/553; G01N 2021/7786; G01N 2021/7773;
(Continued)

(56) References Cited

U.S. PATENT DOCUMENTS 8,242,461 B2 *  8/2012  Rosicke ............ G01N 21/8483
                                                    250/461.1
8,274,034 B2   9/2012  Vogel et al.
(Continued)

FOREIGN PATENT DOCUMENTS

DE   10 2006 030 541 A1   12/2007
DE   10 2007 056 275 B3    4/2009
(Continued)

OTHER PUBLICATIONS

International Search Report (and English translation) and Written Opinion of the International Searching Authority for International Application No. PCT/EP2020/065837 dated Jun. 8, 2020.
(Continued)

*Primary Examiner* — Hoa Q Pham
(74) *Attorney, Agent, or Firm* — Heslin Rothenberg Farley & Mesiti P.C.

(57) ABSTRACT

The invention relates to a sensor module (1) for multiparametric analysis of a medium (105) and to the uses thereof. The sensor module (1) according to the invention is characterised by a combination of photonic and non-photonic measurement principles with parameter-sensitive coatings (103) on a substrate (100). A plurality of properties of a medium (105) can be detected over wide parameter ranges,
(Continued)

wherein the most suitable method can be used for the corresponding parameter, at least for example with regard to the accuracy, the long-term stability, the resolution, the reproducibility, the energy consumption, the manufacturing costs, the necessary space requirements.

22 Claims, 3 Drawing Sheets

(51) Int. Cl.
*C12M 1/34* (2006.01)
*G01N 21/552* (2014.01)
*A61B 5/00* (2006.01)
*G01N 21/78* (2006.01)

(52) U.S. Cl.
CPC ........... *C12M 41/44* (2013.01); *G01N 21/553* (2013.01); *A61B 5/68* (2013.01); *A61B 5/6803* (2013.01); *A61B 5/6861* (2013.01); *G01N 21/78* (2013.01); *G01N 2021/7773* (2013.01); *G01N 2021/7786* (2013.01); *G01N 2201/0628* (2013.01)

(58) Field of Classification Search
CPC .......... G01N 2201/0628; C12M 23/28; C12M 41/44; C12M 41/00; C12M 41/12; A61B 5/68
USPC .................................................. 356/432–440
See application file for complete search history.

(56) References Cited

U.S. PATENT DOCUMENTS

| | | |
|---|---|---|
| 2009/0134309 A1 | 5/2009 | Leo et al. |
| 2012/0162650 A1* | 6/2012 | Wynn ................ G01N 21/8507 250/239 |
| 2014/0001058 A1 | 1/2014 | Ghaffari et al. |
| 2016/0035949 A1* | 2/2016 | Stormberg ............ H05B 45/10 257/88 |
| 2019/0237512 A1 | 8/2019 | Richter et al. |
| 2022/0205924 A1 | 6/2022 | Lau |

FOREIGN PATENT DOCUMENTS

| | | |
|---|---|---|
| DE | 10 2014 010 116 A1 | 8/2015 |
| DE | 10 2016 220 086 A1 | 4/2018 |
| EP | 1 672 356 B1 | 6/2006 |
| EP | 2 955 759 B1 | 12/2015 |
| EP | 2 988 807 B1 | 3/2016 |
| WO | 2011/048472 A1 | 4/2011 |
| WO | 2020/259996 A1 | 12/2020 |

OTHER PUBLICATIONS

Krujatz et al., "Exploiting the Potential of OLED-Based Photo-Organic Sensors for Biotechnological Applications", Chemical Sciences Journal, 2016, vol. 7, Issue 3, 10 pages.

Shinar et al., "Organic Light-emitting Devices (OLEDs) and OLED-Based Chemical and Biological Sensors: An Overview", Journal of Physics D. Applied Physics, 2008, vol. 41, 26 pages.

Coyle et al., "BIOTEX—Biosensing Textiles for Personalised Healthcare Management", IEEE Transactions on Information Technology in Biomedicine, vol. 14, No. 2., Mar. 2010, 7 pages.

* cited by examiner

SENSOR MODULE FOR MULTIPARAMETRICALLY ANALYSING A MEDIUM

CROSS REFERENCE TO RELATED APPLICATIONS

This application is a national stage filing under section 371 of International Application No. PCT/EP2020/065837 filed on Jun. 8, 2020, and published on Dec. 30, 2020 as WO 2020/259996, which claims priority to German Application No. 10 2019 117 045.1, filed on Jun. 25, 2019. The entire contents of WO 2020/259996 are hereby incorporated herein by reference.

FIELD OF THE INVENTION

The invention relates to a sensor module for multiparametric analysis of a medium, having at least one organic light emitter for emitting a photonic signal and at least one device for detecting photonic signals, wherein the at least one organic light emitter and the at least one device for detecting photonic signals are monolithically formed on a semiconductor substrate or in a semiconductor substrate, and furthermore having at least one functional layer system which at least partially covers the at least one organic light emitter and/or the at least one device for detecting photonic signals and is in contact with the medium, wherein the functional layer is designed in such a way that it has at least one active region having at least one property that can be influenced by at least one property of the measuring medium, as well as to the use of the sensor module for multiparametric analysis of a medium.

BACKGROUND OF THE INVENTION

In order to analyse a medium multiparametrically, i.e. on the basis of a plurality of physical, chemical, biochemical and/or biological parameters to be measured quasi-simultaneously, combinations of individual sensors are often used for each one of the parameters, the miniaturisation potential of which is very limited. Further disadvantages are the high energy consumption, the great effort required to improve the signal-to-noise ratio and to ensure electromagnetic compatibility. In particular because of the high production costs, these individual sensor combinations cannot be designed ecologically and economically as inexpensive single-use modules. In current practice, this results in the separation of the transducer and transmitter/processing unit, wherein often only the transducer, sometimes also with transmitter/pre-processing unit, is designed as a disposable item. After an exchange, an adjustment/calibration must be carried out by the customer, which increases the usage costs, sometimes requires additional testing technology and sufficient qualifications, and increases the susceptibility to errors and cross-contamination, for example in critical applications in the pharmaceutical industry.

For example, the simultaneous determination of pH, conductivity, temperature, concentration could be interesting in particular for biological, biochemical or chemical measurement tasks.

From the prior art, for example [Krujatz2016], OLED-based organic photosensors for biotechnological applications are known. Sensors of this type have both organic light-emitting diodes (OLED) as a light source as well as photodetectors and are used as photoluminescence sensors, biosensors or absorption/transmission sensors, for example to determine dissolved oxygen in aqueous solutions, oxygen saturation in the blood or for enzymatic detection of glucose. The OLEDs are applied to substrates such as foils, glass or silicon. Also known are OLED-based sensor arrays for the simultaneous detection of different parameters of the analyte, such as dissolved oxygen, lactate, glucose, etc.

DE 10 2007 056 275 B3 discloses a chip for analysing a medium, organic semiconductors for illuminating the medium and photodetectors being monolithically integrated in a matrix arrangement on an active CMOS substrate. Further active electronic elements can be integrated in the substrate for signal processing.

In DE 10 2006 030 541 A1, an optical arrangement is described, for example for detecting physiological parameters of living beings or for visually displaying information. In this case, at least one organic light-emitting diode and at least one photodiode and/or one CMOS photodiode are preferably arranged or formed on a common substrate and connected to an electronic evaluation and control unit. The arrangement can have further active and passive electronic/electrical components for amplifying, storing and/or controlling the individual elements.

WO 2011/048472 A1 shows an optical sensor system for immunodiagnostics having a layer structure and an OLED as a light source, in which system a fluorescent or phosphorescent marker element binds to an antibody.

EP 1 672 356 B1 discloses an optical sensor for single use, in which sensor a light source and a photodiode are arranged on a substrate and are separated by a separating layer from a functional layer which emits an optical signal based on an analyte.

A sensor device having an OLED as a light source and an acoustic sensor is known from EP 2 988 807 B1.

A MEMS sensor for pressure measurement in CMOS technology is known from DE 10 2014 010 116 B4, the front side of which is in contact with the medium to be measured and offers reliable protection of the sensor against corrosion.

DE 10 2016 220 086 A1 describes a microstructured organic sensor component made up of a multiplicity of sensor segments which are arranged on CMOS substrates. At least one light-emitting diode, each with one or more emitters, can additionally be arranged on the substrate.

EP 2 955 759 B1 discloses a production method for a semiconductor component having a photodetector on a substrate which has a dielectric layer with embedded wiring.

No multiparametric sensor modules are known from the prior art which combine photonic and non-photonic measurement principles with parameter-sensitive coatings on a substrate.

BRIEF SUMMARY OF THE INVENTION

The object of the present invention is therefore to provide a device by means of which a plurality of properties of a medium can be detected over wide parameter ranges using a sensor module, wherein the most suitable method can be used for the corresponding parameter, at least for example with regard to the accuracy, the long-term stability, the resolution, the reproducibility, the energy consumption, the manufacturing costs, the necessary space requirements.

The object is achieved by a sensor module having the features of claim 1. Developments of the invention are specified in the dependent claims.

DETAILED DESCRIPTION OF THE INVENTION

The solution according to the invention is based on the fact that the sensor module advantageously combines photonic and non-photonic measurement principles with one another on the same semiconductor substrate.

In the context of this application, "photonic measurement principles" are understood to mean the use of optical methods and technologies for the detection of photonic signals, it being possible for photonic signals to in principle comprise photons of the entire electromagnetic spectrum, which photons can be converted into electrical signals by means of the measuring technology. According to the invention, the photonic signals comprise in particular photons having wavelengths in the range of visible light or in the range of near infrared light.

In the context of this application, "non-photonic measurement principles" are understood to mean measurement methods that are not based on the detection of photons as information carriers.

The sensor module has at least one organic light emitter, in particular an organic light-emitting diode (OLED), and at least one device for detecting photonic signals (photodetector, PD), which are monolithically formed on or in a semiconductor substrate. In the context of the invention, "monolithic" is to be understood as meaning that the organic light emitter and the device for detecting photonic signals form an inseparable unit with the semiconductor substrate. For example, in various semiconductor processes, for example the CMOS process, component-inherent photodiodes, which can serve as photodetectors, are formed at pn interfaces.

The sensor module furthermore has at least one functional layer system which at least partially covers the at least one organic light emitter and/or the at least one PD and is in direct or indirect contact with the medium to be analysed. The functional layer system is designed in such a way that it has at least one active region having at least one property that can be influenced by at least one property of the medium. This is to be understood as meaning that the at least one active region of the functional layer system contains at least one sensor-active component, the interaction of which with the medium to be analysed influences the response of the sensor-active component to the first photonic signal emitted by the at least one organic light emitter. The sensor-active component emits a second photonic signal that is related to the first photonic signal. The second photonic signal can for example be a (partial) reflection and/or (partial) absorption and/or (partial) scattering/backscattering of the first photonic signal and be intensity-modulated compared to the first photonic signal, or the second photonic signal can for example also be wavelength modulated by fluorescence compared to the first photonic signal. The detection of this photonic response, which contains information about a property of the medium to be analysed, takes place by means of the at least one PD. The sensor-active component of the functional layer system can be, for example, a functional group, a dye, an enzyme, a protein, an antibody, a nucleic acid, a virus or a noble metal cluster. The sensor-active component can also be, for example, a polymer, the swelling behaviour of which is dependent on the pH or the temperature of the medium.

In the context of this application, the term "property" also comprises changes in properties; in particular, the second photonic signal can contain information about absolute and/or relative values of a property of the medium.

The influencing of the photonic response through interaction with the medium can be detected, for example, by luminescence spectroscopy (for example fluorescence spectroscopy), spectrophotometry (for example absorption measurement, reflection measurement), colour measurement (for example ratiometric, photometric, colourimetry/colour change), plasmon resonance (SPR) and/or non-dispersive infrared measurement methods (NDIR).

According to the invention, the semiconductor substrate is furthermore designed in such a way that at least one second property, preferably different from the photonically determined property of the medium, can be determined by means of a non-photonic measurement principle, or the sensor module has at least one component for determining at least one second property, wherein the component is arranged on the semiconductor substrate or a carrier.

The sensor module advantageously offers a highly integrated combination of different sensor technologies. The sensor module according to the invention is suitable for inexpensive mass production using proven semiconductor production technologies. Thus the most suitable method can be used for each parameter to be measured, at least for example with regard to the accuracy, the long-term stability, the resolution, the reproducibility, the energy consumption, the manufacturing costs, the necessary space requirements, while still saving, for example, energy, size and manufacturing costs compared to conventional solutions.

Due to the minimisation of size, energy consumption and costs, it is possible to design the sensor module according to the invention as a disposable item, which advantageously allows factory calibration of all parameters. An effective self-monitoring and/or compensation or referencing is made possible.

Furthermore, the sensor module according to the invention offers the possibility of being able to advantageously select the measurement location from the photonic and non-photonic measurement principle in a simple and advantageous manner.

The functional layer system also acts as a shield for the organic light emitter and PD or semiconductor chip from the environment.

In one embodiment of the device according to the invention, the semiconductor substrate is designed as a CMOS. Using OLED-on-Si-CMOS technology, the integrated CMOS circuit technology can be supplemented by a stable, efficient light emitter, it being possible for the OLED to be arranged monolithically over the CMOS backplane.

In embodiments of the device according to the invention, the semiconductor substrate comprises at least one device for performing an electrochemical measurement or at least one device for performing a temperature measurement or at least one device for performing an impedance measurement or at least one device for performing a magnetic field measurement or at least one device for performing a backscatter measurement or at least one device for performing a flow measurement or at least one device for performing a flow rate measurement or at least one device for performing a heat flow measurement or at least one device for performing a pressure measurement or a combination of the aforementioned. The devices can advantageously be monolithically integrated into the semiconductor substrate. It can also be advantageous for the devices to be integrated into the functional layer system and/or arranged on the functional layer system.

The at least one device for performing an electrochemical measurement preferably comprises an electrode-on-CMOS or ISFET or ChemFET or ENFET or pH-FET or solid-state electrolyte structure or a combination of the aforementioned.

The at least one device for performing a temperature measurement preferably comprises an R-on-CMOS sensor or a thermocouple sensor or a semiconductor sensor or a combination of the aforementioned.

The at least one device for performing an impedance measurement preferably comprises an interdigital electrode structure.

The at least one device for performing a magnetic field measurement preferably comprises a Hall sensor.

The at least one device for performing a flow rate measurement preferably comprises the principle of a hot wire anemometer.

The at least one device for performing a heat flow measurement preferably comprises a thermopile sensor.

The at least one device for performing a pressure measurement preferably comprises a thin-film sensor or a thick-film sensor or a piezoresistive sensor or a MEMS sensor or a combination of the aforementioned.

In a further preferred embodiment, the sensor module according to the invention has a plurality of organic light emitters, which are spatially separated from one another at definable positions or can be arranged in the semiconductor substrate, and which each emit a first photonic signal, it being possible for the wavelengths of the first photonic signals of different organic light emitters to be different from one another or to be the same. The plurality of organic light emitters can be arranged in segments or arrays.

In a further preferred embodiment, the sensor module according to the invention has a plurality of devices for detecting photonic signals which are spatially separated from one another at definable positions or can be arranged in the semiconductor substrate. The plurality of devices for detecting photonic signals can be designed in such a way that they have spectral sensitivity ranges that differ from one another, so that devices that differ from one another can detect photonic signals of different wavelengths. The plurality of devices for detecting photonic signals can, however, also be designed in such a way that they have the same sensitivity ranges or overlapping sensitivity ranges, the assignment of the corresponding detected second photonic signal to the location of the emission thereof taking place via distinguishable overlaps of the numerical apertures. The plurality of devices for detecting photonic signals can also be arranged in segments or arrays.

The configuration of the sensor module according to the invention with a plurality of organic light emitters and a plurality of devices for detecting photonic signals advantageously offers the possibility of spatially resolved analysis of the medium, and this particularly advantageously even with a small active region of the functional layer system. In the context of this invention, "spatially resolved" is understood to mean the assignment of detected signals to a measurement location or location of origin.

Various concepts of spatial resolution in relation to the sensor module according to the invention are explained in more detail below.

On the one hand, an active region of the functional layer system can have a plurality of sensor-active components, for example dyes, which are excited by means of organic light emitters that differ from one another and emit first photonic signals with wavelengths that differ from one another and emit second photonic signals with wavelengths that differ from one another and are detected by the corresponding PDs that differ from one another with spectral sensitivity ranges that differ from one another.

On the other hand, it can also be the case that the plurality of sensor-active components of an active region of the functional layer system are excited differently, but emit second photonic signals in the same sensitivity range. In this case, an assignment of the second photonic signals detected by means of PDs that differ from one another to the location of their emission, in particular to one of the sensor-active components, can take place via the numerical aperture of the optical system made up of light emitters/sensor-active components/PD.

Furthermore, in the present case, a time-delayed excitation of the sensor-active components can also take place, or a mixture/superposition of the second photonic signals can be detected.

In a further preferred embodiment of the sensor module according to the invention, at least one device for detecting photonic signals is arranged directly below at least one organic light emitter. In this configuration, the emitted first photonic signal for referencing, for example, intensity and/or phase fluctuations can advantageously be measured directly.

For the purpose of referencing the sensor module, at least one combination of measured values generated with the aid of two second photonic signals or two non-photonic signals or a second photonic and a non-photonic signal can be used. The location allocation of the organic light emitter and PD on the sensor module according to the invention particularly advantageously allows for referencing directly at the position to be referenced.

In a further preferred embodiment of the sensor module according to the invention, the functional layer system has more than one active region, the active regions being arranged spatially separated from one another. The spatial separation also comprises an arrangement of a plurality of active regions one above the other, i.e. in the same optical path between the organic light emitter and the device for detecting photonic signals.

On the one hand, the active regions can contain the same sensor-active components and be sensitive to the same property of the medium. Due to the spatial separation of the active regions, a spatially resolved analysis of the medium with regard to a certain property is possible in this configuration.

On the other hand, the active regions can be designed in such a way that they are sensitive to properties that differ from one another. This can be implemented, for example, using different sensor-active components, or in that at least one of the plurality of active regions has a defined coating. The sensor module according to the invention thus advantageously allows the multiparametric analysis of the medium in a particularly compact, simple and miniaturised manner.

The plurality of active regions of the functional layer system can also have spectral sensitivities that differ from one another, wherein the spectral regions in which the sensor-active components of different active regions can be photonically excited can overlap. This embodiment can advantageously be combined with the inventive embodiment of the sensor module having a plurality of organic light emitters and a plurality of devices for detecting photonic signals.

An advantageous embodiment comprises the excitation of a lower active region of a plurality of active regions of the functional layer system arranged one below the other by means of a first photonic signal, this lower active region emitting a second photonic signal (which generally comprises a different wavelength range) to a further active region arranged thereabove in the optical path, whereby sensor-active components are excited in this further active region, and a third photonic signal, modulated by the changes in properties of this further active region caused by at least one property of the surrounding medium, is emitted, at least the regions/layers of the functional layer system arranged between the semiconductor substrate and this further active region being transparent for this third photonic signal, so that this signal, in this case referred to as the third photonic signal, can be received by at least one photodiode.

In summary, the sensor module according to the invention offers the possibility of spatially resolved analysis in two aspects:

- On the one hand with regard to the medium, i.e. the detected second photonic signal and/or the non-photonic signal can be assigned to the measurement location in the medium and describe(s) the property of the medium at this location;
- On the other hand, in the internal allocation of the transmitted first photonic signal and the detected second photonic signal by using the numerical aperture (NA).

In a further embodiment, the functional layer system of the sensor module according to the invention comprises at least one functional layer which is arranged on a functional layer carrier. The functional layer system can be built up from a plurality of layers, of which only one or more have active regions.

In general, the functional layer carrier is transparent to the wavelength of the first and the second photonic signal. In particular, the functional layer carrier can be designed as an optical lens or as an optical lens array or as an optical filter or as an optical grating or as a combination of the aforementioned. The functional layer carrier can be arranged directly on the semiconductor substrate or at a distance therefrom. The functional layer carrier can also be designed as part of a housing accommodating the semiconductor substrate or encapsulate/seal the semiconductor substrate (including possible structures) by direct joining processes (for example gluing, anodic bonding, adhesive bonding, casting). This advantageously allows for an effective, for example non-parasitic, luminescent module encapsulation.

In a further embodiment, the sensor module according to the invention has at least one device for storing data, for example measurement data, program code, logbook data, history data, and/or for evaluating and influencing data, for example for compensating and/or transmitting data, for example measurement data, evaluation data, status information, data logger data and/or for communication. Transmission and communication can be digital and/or analogue, wired or wireless. The sensor module can also work autonomously and the measurement data can be read out after the measurement has been completed.

In a further embodiment, the sensor module according to the invention has at least one device for controlling and/or modulating/demodulating the at least one organic light emitter and/or the at least one device for detecting photonic signals.

The aforementioned devices are preferably formed monolithically in the semiconductor substrate.

In a further embodiment, the sensor module according to the invention has at least one device for providing the electrical energy to be used for operating the sensor module. This can be, for example, a battery or supercapacitor. The device can also be suitable for converting other forms of energy into electrical energy, for example potential energy of sound, kinetic energy or thermal energy, as commonly known as energy harvesting. Furthermore, the energy can be transmitted wirelessly, for example by standards such as NFC or QI, or induced by field coupling. The sensor module can thereby advantageously work autonomously.

In a further embodiment, the sensor module according to the invention has at least one actuating component, for example a heater for temperature control, in particular thermal stabilisation, of the sensor module or for activating enzymes in the functional layer system, or actuating components for controlling microfluidics. Advantageously, the actuator system in the sensor module according to the invention can be integrated into the smallest space in an energy-efficient manner and in a reaction-accelerated manner. Due to the compact design, the thermal stabilisation of the sensor module can be carried out in an energy-efficient manner and with short control times.

Furthermore, a plurality of sensor modules according to the invention can be combined with a base module, for example in a cubic arrangement, and use within the base module, for example, a common power supply, data processing, data storage or communication, wherein the sensor modules can be mounted to be separately replaceable or modular.

The small and compact design of the sensor modules according to the invention allows faster reaction times, faster response times and shorter settling times of the sensor module combination.

The sensor module according to the invention is preferably used in a lab-on-a-chip system. For this purpose, microfluidics can be coupled directly or indirectly to the functional layer system, or the microfluidics can be a structural part of the semiconductor substrate or the functional layer system.

The sensor module according to the invention can advantageously be designed to be sterilisable or disinfectable in a simple manner. This results in further preferred uses.

The use of the sensor module according to the invention for fermentation monitoring, in particular in a disposable fermentation bag, is furthermore preferred. These are already sterilised at the factory by the manufacturer, usually with gamma radiation. The subsequent introduction of measurement technology to detect the control parameters is cumbersome and can result in subsequent contamination of the disposable fermentation bag. Therefore, in the pharmaceutical industry, for example, extensive procedures have to be carried out to check the clean-up, which are expensive, time-consuming and in turn involve the risk of cross-contamination. Because the sensor module according to the invention can be sterilised, it can be placed in the disposable fermentation bag before sterilisation. The sensor module according to the invention is inexpensive and biocompatible, and can be disposed of or recycled easily and without damage to the environment, so that it can advantageously be used as a disposable item. In addition to gamma sterilisation, other disinfection and sterilisation options are available, for example by means of disinfectants, by autoclaving (steam-sterilisable), by plasma sterilisation, by UV radiation.

The use of the sensor module according to the invention for monitoring vital parameters is furthermore preferred. This includes for example the measurement of the $CO_2$ and/or $O_2$ concentration in the breath, glucose and/or lactate concentration in saliva. A particularly advantageous combination of parameters can be obtained through transcutaneous measurements of the $CO_2$ and/or $O_2$ partial pressure using a photonic measurement principle and temperature and pH measurements on the skin using a non-photonic measurement principle.

The monitoring of various vital parameters is becoming increasingly important in the fitness sector. It could be shown, for example, that overweight patients lose more weight with a personalised nutrition program if their nutrition plan is adapted to the measured oxygen consumption (detection and analysis of metabolic parameters; metabolic).

Another important field of application is in medical technology. Metabolic diseases such as diabetes can advantageously be detected by means of the sensor module according to the invention, or enzymatic disorders or disorders of the intestinal flora can be examined continuously over a longer period of time.

To increase patient safety, for example during surgery or during intensive monitoring, obtaining representative samples of the internal partial gas exchange of the lungs is very desirable. The sensor module according to the invention offers for example the combination of an ultra-fast oxygen and/or carbon dioxide partial pressure sensor ($pO_2$ and/or $pCO_2$) with the measurement of the flow of breathing gases at the airway opening and thus provides this highly desirable and crucial information, which then, for example, can be used to optimise the ventilator settings for intensive care patients and patients under anaesthesia.

$CO_2$ and $O_2$ are gases that easily diffuse through body and skin tissue and can therefore be measured using a corresponding non-invasive sensor that is attached to the surface of the skin. For transcutaneous measurements, the sensor module according to the invention can be arranged on a carrier that can be applied to the skin.

The sensor module according to the invention can be arranged on a dental brace, a nose clip or a bite guard.

Or the sensor module can be integrated in a ventilator and/or anaesthesia device and/or a lung function device.

Furthermore, the sensor module according to the invention can be arranged on a collecting vessel for urine and stool samples as well as blood samples.

In the context of this application, the arrangement also comprises embodiments in which the sensor module is embedded in the aids mentioned above so that it is accessible to the medium.

When using the sensor module according to the invention for monitoring vital parameters, the sensor module can advantageously be implanted in animals or humans.

In a further embodiment, the sensor module according to the invention can be packaged as a capsule for swallowing. This allows better passage through the gastrointestinal tract.

The uses according to the invention of the sensor module according to the invention offer a plurality of advantages, some of which are listed below.

Due to the low acquisition costs and the possibility of factory calibration/adjustment and sterilisation, the sensor module according to the invention can be designed as a disposable item and disposed of with the urine, blood or stool samples, which also minimises the risk of cross-contamination.

The multiparametric analysis of the medium allows parallel real-time or online monitoring of various vital parameters.

The uses according to the invention can be designed non-invasively; no analyte is consumed.

Compared to the conventional electrochemical oxygen sensors, the sensor module on which the invention is based is more environmentally friendly since the high proportions of lead currently used in $O_2$ sensor technology are avoided.

Due to the ultra-fast response times (<50 ms rise time of 10%-90%) and small size (<1 ml, <25 g), the low energy consumption and the low heat loss, vital parameters can be monitored directly in the main breathing flow, for example, without endangering patient safety or presenting a risk of ignition in the case of flammable or explosive analytes, cleaning agents or anaesthetics (explosion protection, ATEX).

The sensor module can be sterilised, for example by gamma radiation, plasma sterilisation, autoclaving, sterilising cleaning agents.

The sensor module according to the invention can be designed to be powered autonomously. It offers the possibility of radio communication, is ultra-compact and has the lowest power losses, can detect photonic and non-photonic sensory parameters, has integrated methods for referencing, and the functional layer can at the same time represent part of the encapsulation to the medium, which facilitates miniaturisation.

The invention is not limited to the embodiments illustrated and described, but also comprises all embodiments which have the same effect within the context of the invention. Furthermore, the invention is also not limited to the feature combinations specifically described, but may also be defined by any other combination of specific features of any of the individual features disclosed as a whole, provided that the individual features are not mutually exclusive or that a specific combination of individual features is not explicitly excluded.

In the following, the invention will be explained based on embodiments without being limited thereto.

In the tables and drawings:

Table 1 shows examples of photonic measurement principles for determining various properties of a medium and examples for the sensor-active component;

Table 2 shows examples of non-photonic measurement principles for determining various properties of a medium and examples of devices for measuring the property.

TABLE 1

| | | |
|---|---|---|
| Examples of photonic measurement principles | | |
| Property of the medium | Measurement principle/ measurement method | Sensor-active component |
| Dissolved oxygen | Photonic/ fluorescence measurement | Organic dye (e.g. PtTFPL in PSAN or PtTFPP in polystyrene) |
| pH | Photonic/ fluorescence measurement | Organic dye (e.g. HPTS, seminaphtharhodafluor (SNARF), hydroxycoumarin) |

TABLE 1-continued

Examples of photonic measurement principles

| Property of the medium | Measurement principle/ measurement method | Sensor-active component |
|---|---|---|
| Temperature | Photonic/ fluorescence measurement | Organic dye (e.g. rhodamine, or $Eu(tta)_3(dpbt)$ in PVC) |
| Dissolved $CO_2$ | Photonic/ fluorescence measurement | Organic dye (e.g. HPTS) in combination with a gas-permeable and proton-impermeable polymer (e.g. Teflon, silicone or polytetrafluoroethylene (PTFE)) |
| Glucose | Photonic/ fluorescence measurement | Organic dye (e.g. PtTFPL or PtTFPP) in combination with glucose oxidase enzyme (glucose oxidase) |
| Lactate | Photonic/ fluorescence measurement | Organic dye (e.g. PtTFPL or PtTFPP) in combination with lactate oxidase |
| Pressure | Photonic/ fluorescence measurement | Organic dye (e.g. PtTFPL or PtTFPP in FIB) |
| Toxin measurement | Photonic/ fluorescence measurement | GFP protein in the GFP gene |
| Toxin measurement | Photonic/ SPR measurement | Ion channel on a thin, noble metal layer/layer system |
| Refractive index | Photonic/ SPR measurement | Thin, noble metal layer/layer system (e.g. Ag, Au) |
| Hydrogen | Photonic/ SPR measurement | Noble metal layer/layer system (e.g. palladium layer) |
| pH | Photonic/ colorimetric measurement | Colorimetric indicators; e.g. bromophenol blue [bromocresol purple]) |
| Carbon monoxide | Photonic/ colorimetric measurement | Colorimetric indicators (e.g. binuclear rhodium complex) |
| Nitrogen dioxide | Photonic/ colorimetric measurement | Colorimetric indicators (e.g. N,N,N',N'-tetramethyl-pphenylenediamine; quinones) |
| Ammonium | Photonic/ ratiometric fluorescence measurement | Organic dye (e.g. Oxazine 170 perchlorate for ammonium, Oxazine170 perchlorate-ethyl cellulose (O17-EC) membrane with aluminium-containing compounds for nitrate measurement) |
| SpO2 | Photonic/ Ratiometric absorption measurement | 2-wavelength reflex pulse oximetry |

TABLE 2

Examples of non-photonic measurement principles

| Property of the medium | Measurement principle/ measurement method | Device |
|---|---|---|
| pH | Non-photonic/ electrochemical measurement | Electrode arrangement with, for example, a metal oxide layer as the working electrode (for example iridium oxide, ruthenium oxide), silver/silver chloride as reference electrode); ISFET |
| Temperature | Non-photonic/ bandgap voltage reference | Brokaw cell Platinum thick-layer sensor R-on-CMOS |
| Cell growth/ cell death | Non-photonic/ Impedance measurement method | Interdigital electrode structure |
| Dissolved $CO_2$ | Non-photonic/ potentiometric measurement principle | Electrode arrangement in combination with a gas-permeable and proton-impermeable polymer (e.g. Teflon, silicone or polytetrafluoroethylene (PTFE)) |

TABLE 2-continued

Examples of non-photonic measurement principles

| Property of the medium | Measurement principle/ measurement method | Device |
|---|---|---|
| Glucose | Non-photonic/amperometric measurement | 2- or 3-electrode arrangement in combination with the enzyme glucose oxidase |
| Lactate | Non-photonic/ amperometric measurement | 2- or 3-electrode arrangement in combination with the enzyme lactate oxidase |
| Pressure | Non-photonic/ | thin-film sensor, thick-film sensor, piezoresistive sensor, MEMS sensor |

When combining the at least one photonic measurement principle with a device for temperature measurement, the advantage of the sensor module according to the invention that the measurement location of the desired parameters can be selected relatively freely can be used particularly favourably, in that, for example, an R-on-CMOS sensor can be arranged directly next to a detection structure for fluorescent light, so that the correction variable "temperature" of the associated fluorescent dye can be detected without a large delay or transfer characteristic.

Figure 1:
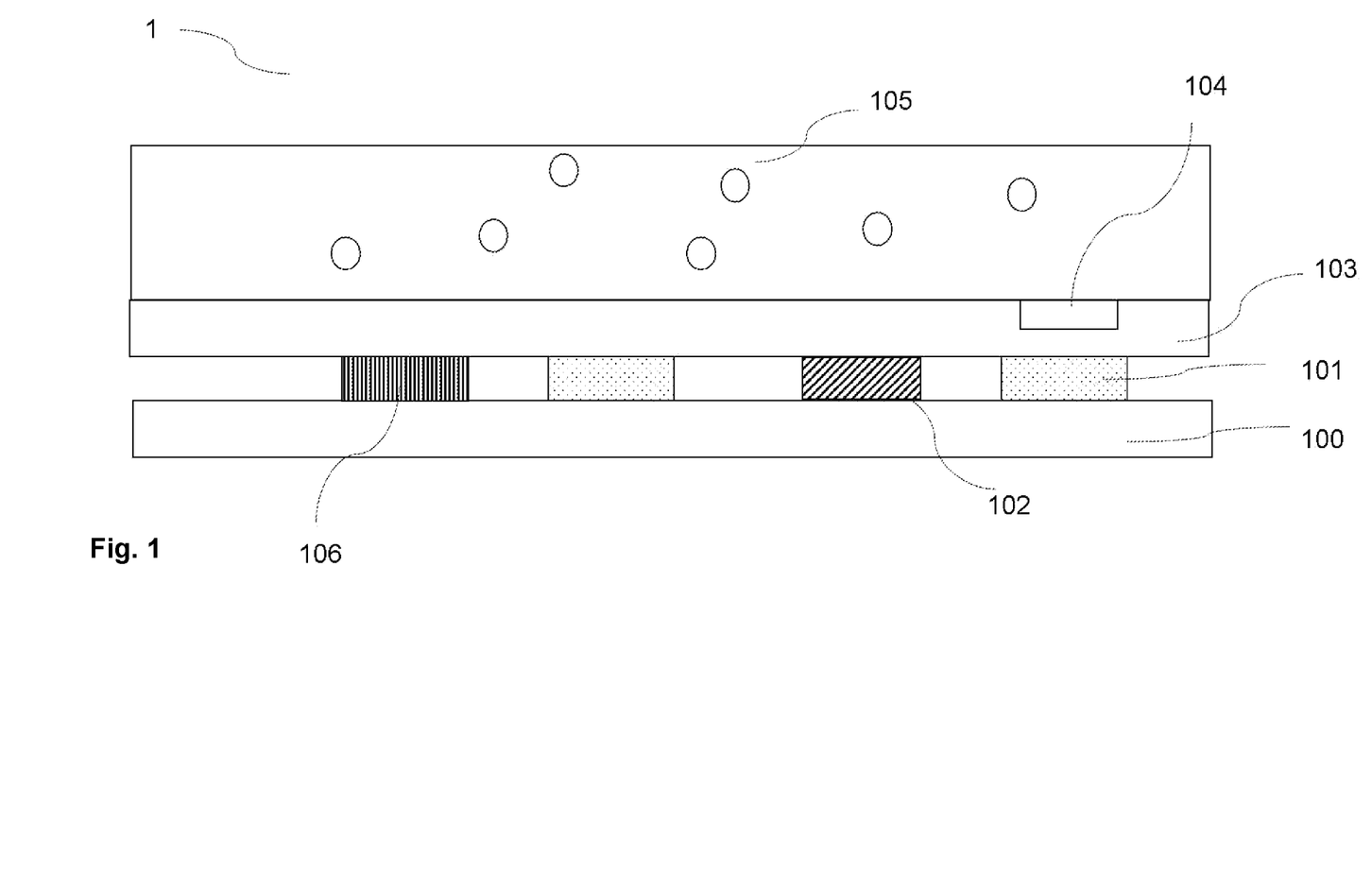
FIG. 1 is a schematic side view of a sensor module according to the invention for multiparametric analysis of a medium.

FIG. 1 is a schematic side view of a sensor module 1 according to the invention for multiparametric analysis of a medium 105. The sensor module 1 has at least one organic light emitter for emitting a first photonic signal 101 and at least one device for detecting photonic signals 102. The organic light emitter 101 and the device for detecting photonic signals 102 are formed monolithically on a semiconductor substrate 100 which is advantageously formed as a CMOS semiconductor substrate. Furthermore, the sensor module 1 has at least one functional layer system 103 which covers the at least one organic light emitter 101 and/or the at least one device for detecting photonic signals 102 and is in contact with the medium 105. The functional layer system 103 has at least one active region 104. The sensor module 1 has a component for determining a second property by means of a non-photonic measurement principle 106, which component is arranged on the semiconductor substrate 100.

Furthermore, the sensor module 1 advantageously has at least one device for storing data and/or for evaluating and influencing data and/or for transmitting data and/or for communication and/or at least one device for controlling and/or modulating/demodulating the at least one organic light emitter and/or the at least one device for detecting photonic signals 107. Furthermore, the sensor module 1 advantageously has a device for providing the electrical energy 108 to be used for operating the sensor module 1.

Figure 2:
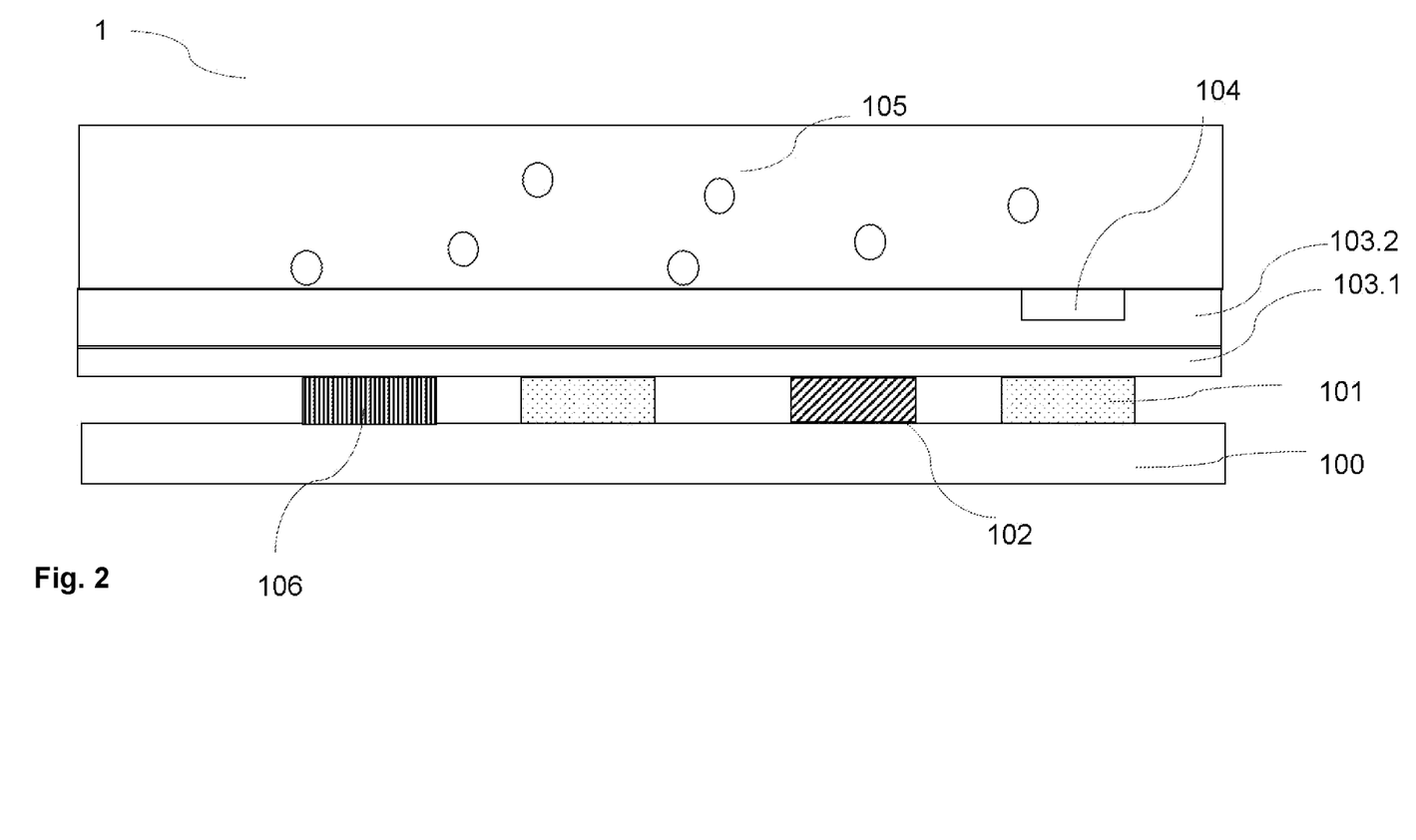
FIG. 2 is a schematic side view of an embodiment of a sensor module according to the invention for multiparametric analysis of a medium.

FIG. 2 is a schematic side view of an embodiment of the sensor module 1 according to the invention for multiparametric analysis of a medium 105. The sensor module 1 corresponds to the sensor module from FIG. 1. The functional layer system 103 has a functional layer carrier 103.1 and a functional layer 103.2. The functional layer carrier 103.1 can be designed as an optical lens or as an optical lens array or as an optical filter or as an optical grating or as a combination of the aforementioned.

Figure 3:
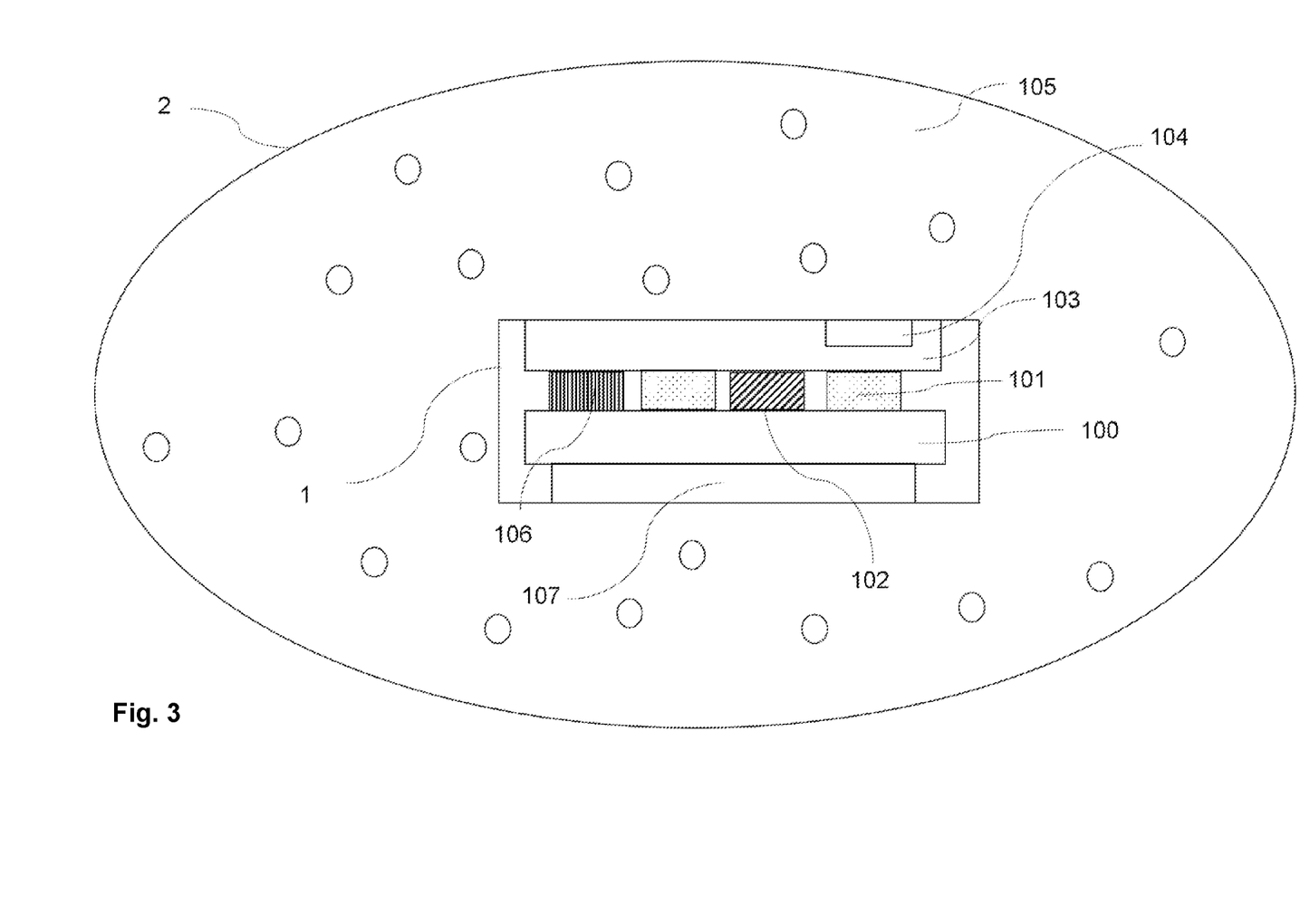
FIG. 3 shows a sensor module according to the invention in a fermentation chamber.

FIG. 3 shows schematically a sensor module 1 in a fermentation reactor 2 which is filled with a medium 105. The sensor module 1 corresponds to the sensor module 1 shown in FIG. 1. It can be seen that the functional layer system 103 is in contact with the medium 105 and shields the organic light emitter 101 and the device for detecting photonic signals 102 from the medium 105. The sensor module 1 has at least one device for storing data and/or for evaluating and influencing data and/or for transmitting data and/or for communication 107. Furthermore, the sensor module 1 can have at least one device for controlling and/or modulating/demodulating the at least one organic light emitter and/or the at least one device for detecting photonic signals (not shown). The sensor module 1 can furthermore have a device for providing the electrical energy to be used for operating the sensor module (not shown).

LIST OF REFERENCE SIGNS

1 Sensor module
100 Semiconductor substrate
101 Organic light emitter
102 Device for the detection of photonic signals
103 Functional layer system
103.1 Functional layer carrier
103.2 Functional layer
104 Active region
105 Medium
106 Component for determining at least one second property
107 Device for storing data and/or for evaluating and influencing data and/or for transmitting data and/or for communication
2 Fermentation reactor

CITED NON-PATENT LITERATURE

[Krujatz2016] Krujatz F. et al "Exploiting the Potential of OLED-Based Photo-Organic Sensors for Biotechnological Applications"; Chem Sci J 2016 Vol. 7, Issue 3, 1000134, DOI: 10.4172/2150-3494.1000134

The invention claimed is:
1. Sensor module for multiparametric analysis of a medium, comprising
at least one organic light emitter for emitting a first photonic signal and
at least one device for detecting photonic signals, said device for detecting photonic signals being a detector;
wherein the at least one organic light emitter and the at least one device for detecting photonic signals are monolithically formed on a semiconductor substrate or in a semiconductor substrate;
at least one functional layer system which at least partially covers the at least one organic light emitter and/or the at least one device for detecting photonic signals and is in contact with the medium, wherein the functional layer system is in the form of a layer having at least one active region having at least one property that can be influenced by at least one property of the medium characterised in that the at least one active region of the functional layer system can be photonically excited by means of the at least one organic light emitter and emits a second photonic signal which is detected by the at least one device for detecting photonic signals, the second photonic signal containing information about the at least one property of the medium, and in that the semiconductor substrate is able to determine at least one second property by means of a non-photonic measurement principle or the sensor module has at least one component for determining at least one second property, which module is arranged on the semiconductor substrate or a carrier.

2. Sensor module according to claim 1, characterised in that the semiconductor substrate is designed as a CMOS.

3. Sensor module according to claim 1, characterised in that the semiconductor substrate comprises at least one device for performing an electrochemical measurement or at least one device for performing a temperature measurement or at least one device for performing an impedance measurement or at least one device for performing a magnetic field measurement or at least one device for performing a backscatter measurement or at least one device for performing a flow measurement or at least one device for performing a flow rate measurement or at least one device for performing a heat flow measurement or at least one device for performing a pressure measurement or a combination of the aforementioned.

4. Sensor module according to claim 3, characterised in that the at least one device for performing an electrochemical measurement comprises an electrode-on-CMOS or ISFET or ChemFET or ENFET or pH-FET or solid-state electrolyte structure or a combination of the aforementioned.

5. Sensor module according to claim 3, characterised in that the at least one device for performing a temperature measurement comprises an R-on-CMOS sensor or a thermocouple sensor or a semiconductor sensor or a combination of the aforementioned.

6. Sensor module according to claim 3, characterised in that the at least one device for performing a impedance measurement comprises an interdigital electrode structure.

7. Sensor module according to claim 3, characterised in that the at least one device for performing a magnetic field measurement comprises a Hall sensor.

8. Sensor module according to claim 3, characterised in that the at least one device for performing a flow rate measurement comprises the principle of a hot wire anemometer.

9. Sensor module according to claim 3, characterised in that the at least one device for performing a heat flow measurement comprises a thermopile sensor.

10. Sensor module according to claim 3, characterised in that the at least one device for performing a pressure measurement comprises a thin-film sensor or a thick-film sensor or a piezoresistive sensor or a MEMS sensor or a combination of the aforementioned.

11. Sensor module according to claim 1, characterised in that the sensor module has a plurality of organic light emitters which can be arranged spatially separated from one another at definable positions and which each emit a first photonic signal having wavelengths that differ from one another or each emit a first photonic signal having the same wavelength.

12. Sensor module according to claim 1, characterised in that the sensor module has more than one device for detecting photonic signals which can be arranged spatially separated from one another at definable positions, the devices for detecting photonic signals having spectral sensitivity ranges that differ from one another, so that they each detect a second photonic signal having wavelengths that differ from one another, or the devices for detecting photonic signals having the same sensitivity ranges or overlapping sensitivity ranges, the assignment of the corresponding detected second photonic signal to the location of the emission thereof taking place via distinguishable numerical apertures.

13. Sensor module according to claim 1, characterised in that at least one device for detecting photonic signals is arranged directly below at least one organic light emitter.

14. Sensor module according to claim 1, characterised in that the functional layer system has more than one active region, the active regions being arranged spatially separated from one another.

15. Sensor module according to claim 14, characterised in that the active regions of the functional layer system are designed so that the second photonic signals emitted by separate active regions contain information about various properties of the medium.

16. Sensor module according to claim 1, characterised in that the functional layer system comprises at least one functional layer which is arranged on a functional layer carrier.

17. Sensor module according to claim 16, characterised in that the functional layer carrier is designed as an optical lens or as an optical lens array or as an optical filter or as an optical grating or as a combination of the aforementioned.

18. Sensor module according to claim 1, characterised in that the sensor module has at least one device for storing data and/or for evaluating and influencing data and/or for transmitting data and/or for communication.

19. Sensor module according to claim 1, characterised in that the at least one device is formed monolithically in the semiconductor substrate.

20. A lab-on-a-chip system comprising the sensor module according to claim 1.

21. A method for monitoring vital parameters comprising using the sensor module according to claim 1 to measure one or more analytes.

22. The method according to claim 21, wherein the sensor module is designed to be implantable.

* * * * *